(12) United States Patent
Chen (10) Patent No.: US 6,933,377 B2
(45) Date of Patent: Aug. 23, 2005

(54) COMPOSITIONS COMPRISING MULTIPLE IMMUNODEFICIENCY VIRUS SUBUNITS FOR INDUCING AN IMMUNE RESPONSE

(76) Inventor: Qun Chen, 1202 44th Ave., San Francisco, CA (US) 94122

(*) Notice: Subject to any disclaimer, the term of this patent is extended or adjusted under 35 U.S.C. 154(b) by 38 days.

(21) Appl. No.: 10/207,346

(22) Filed: Jul. 29, 2002

(65) Prior Publication Data
US 2004/0018207 A1 Jan. 29, 2004

(51) Int. Cl.$^7$ .............................................. C07H 21/04
(52) U.S. Cl. ................................ 536/23.72; 435/235.1; 435/236; 435/320.1
(58) Field of Search .................... 536/23.72; 435/235.1, 435/236, 320.1

(56) References Cited

U.S. PATENT DOCUMENTS

| 4,683,195 A | 7/1987 | Mullis |
| 4,683,202 A | 7/1987 | Mullis |
| 4,965,188 A | 10/1990 | Mullis |

OTHER PUBLICATIONS

Rifkin et al. "A single amino–acid change between the antigenically different extracellular serine proteases V2 and B2 from *Dichelobacter nodosus*", Gene, vol. 167 (1995), pp. 279–283.*
Abaza et al. "Effects of amino acid substitutions outside an antigenic site on protein binding to monoclonal antibodies of predetermined specificity obtained by peptide immunization", Journal of Protein Chemistry, vol. 11, No. 5 (1992), pp 433–444.*
Cruse et al. Illustrated Dictionary of Immunology (Boca Raton, FL, CRC Press, Inc., 1995), p. 309. QR180.4.C78.*
Paul, Fundamental Immunology, (Philadelphia & New York, Lippincott–Raven Publishers, 1993), pp. 250 and 1311–1312. QR181.F84.*
Aldovini and Young, "Mutations of RNA and protein sequences involved in human immunodeficiency virus type 1 packaging result in production of noninfectious virus," *J. Virol.,* 64:1920–1926 [1990].
Ausubel et al., *Current Protocols in Molecular Biology,* Greene Publishing Associates and Wiley Interscience, N.Y. [1989] copyright pages only.
Baba et al., "Live attenuated, multiply deleted simian immunodeficiency virus cases AIDS in infant and adult macaques," *Nat. Med.,* 5:194–203 [1999].
Benson et al., "Recombinant vaccine–induced protection against the highly pathogenic simian immunodeficiency virus SIVmac251: dependence on route of challenge exposure," *J. Virol.,* 72:4170–4182 [1998].
Bernstein et al., "Oligomerization of the hydrophobic heptad repeat of gp41", *J. Virol.,* 69:2745–2750 [1995].
Cheng et al., "Coexpression of the simian immunodeficiency virus Env and Rev proteins by a recombinant human adenovirus host range mutant," *J. Virol.,* 66:6721–6727 [1992].
Clavel and Orenstein, "A mutant of human immunodeficiency virus with reduced RNA packaging and abnormal particle morphology," *J. Virol.,* 64:5230–5234 [1990].
Collman et al., "An infectious molecular clone of an unusual macrophage–tropic and highly cytopathic strain of human immunodeficiency virus type 1," *J. Virol.,* 66:7517–7521 [1992].
Emerman and Malim, "HIV–1 regulatory/accessory genes: keys to unraveling viral and host cell biology," *Science,* 280:1880–1884 [1998].
Ferco et al., "Hyperattenuated recombinant influenza a virus nonstructural–protein–encoding vectors induce human immunodeficiency virus type 1 Nef–specific systemic and mucosal immune responses in mice," *J. Virol.,* 75:8899–8908 [2001].
Franchini et al., "Sequence of simian immunodeficiency virus and its relationship to the human immunodeficiency viruses," *Nature,* 328:539–543 [1987].
Gailer et al., "The yellow fever 17D vaccine virus: molecular basis of viral attenuation and its use as an expression vector," *Brazilian J. Med. Biol. Res.,* 30:157–168 [1997] abstract only.
Galli et al., "Th1 and Th2 responses, HIV–1 coreceptors, and HIV–1 infections," *J. Biol. Regul. Homeost. Agents,* 15:308–313 [2001] abstract only.
Gallo et al., "HIV/HTLV gene nomenclature," *Nature,* 333:504 [1988].
Gorse et al., "HIV type 1 vaccine–induced t cell memory and cytotoxic t lymphocyte responses in HIV type 1–uninfected volunteers," *AIDS Res. Hum. Retroviruses,* 17:1175–1189 [2001].
Gottlinger et al., "Role of capsid precursor processing and myristoylation in morphogenesis and infectivity of human immunodeficiency virus type 1," *Proc. Natl. Acad. Sci., USA,* 86:5781–5785 [1989].
Graham et al., "Safety and immunogenicity of a candidate HIV–1 vaccine in healthy adults: recombinant glycoprotein (rgp)120," *Ann. Intern. Med.,* 125:270–279 [1996].
Hu et al., "The emerging genetic diversity of HIV: the importance of global surveillance for diagnostics, research, and prevention," *JAMA,* 275:210–216 [1996].
Jacks et al., "Characterization of ribosomal frameshifting in HIV–1 gag–pol expression," *Nature,* 331:280–283 [1988].
Kobayashi et al., "Immunostimulatory DNA prepriming: a novel approach for prolonged Th1–biased immunity," *Cell Immunol.,* 198:69–75 [1999].
Korber et al., "Limitations of a molecular clock applied to considerations of the origin of HIV–1," *Science,* 280:1868–1871 [1998].

(Continued)

*Primary Examiner*—Jeffrey Stucker
(74) *Attorney, Agent, or Firm*—Medlen & Carroll, LLP

(57) ABSTRACT

The present invention relates to prophylactic and therapeutic acquired immunodeficiency syndrome vaccines. In particular, the present invention provides methods and compositions utilizing recombinant HIV-1, HIV-2 and/or SIV genes or gene products in safe vaccination approaches.

12 Claims, 5 Drawing Sheets

OTHER PUBLICATIONS

Kumar et al., "A recombinant BCG vaccine generates a Th1–like response and inhibits IgE synthesis in BALB/c mice," *Immunol.*, 97:515–521 [1999].

Lever et al., "Identification of a sequence required for efficient packaging of human immunodeficiency virus type 1 virus RNA into virions," *J. Virol.*, 63:4085–4087 [1989].

Levy, "Pathogenesis of human Immunodeficiency virus infection," *Microbiol. Rev.*, 57:183–289 [1993] abstract only.

Lewis et al., "Identification of a cis–acting element in human immunodeficiency virus type 2 (HIV–2) that is responsive to the HIV–1 rev and human T–cell leukemia virus types I and II rex proteins," *J. Virol.*, 64:1690–1697 [1990].

Mellors et al., "Plasma viral load and $CD4^+$ lymphocytes markers of HIV–1 infection," *Ann. Intern. Med.*, 126:946–954 [1997].

Miller et al., "*Rhesus macaques* previously infected with simian/human immunodeficiency virus are protected from vaginal challenge with pathogenic SIVmac239," *J. Virol.*, 71:1911–1921 [1997].

Monath et al., "Recombinant, chimaeric live, attenuated vaccine (ChimeriVax™) incorporating the envelope genes of Japanese encephalitis (SA14–14–2) virus and the capsid and nonstructural genes of yellow fever (17D) virus is safe, immunogenic and protective in non–human primates," *Vaccine*, 17:1869–1882 [1999].

Mooij and Heeney, "Rational development of prophylactic HIV vaccines based on structural and regulatory proteins," *Vaccine*, 20:304–321 [2002].

Muesing et al., "Nucleic acid structure and expression of the human AIDS/lymphadenopathy retrovirus," *Nature*, 313:450–458 [1985].

Pang et al., "High level of unintegrated HIV–1 DNA in brain tissue of AIDS dementia patients," *Nature*, 343:85–89 [1990].

Perelson et al., "HIV–1 dynamics in vivo: virion clearance rate, infected cell life–span, and viral generation time," *Science*, 271:1582–1586 [1996].

Purvis et al., "HIV type 1 Tat protein induces apoptosis and death in Jurkat cells," *AIDS Res. Hum. Retroviruses*, 11:443–450 [1995].

Pushko et al., "Replicon–helper systems from attenuated venezuelan equine encephalitis virus: expression of heterologous genes in vitro and immunization against heterologous pathogens in vivo," *Virology*, 239:389–401 [1997].

Regier and Destrosiers, "The complete nucleotide sequence of a pathogenic molecular clone of simian immunodeficiency virus," *AIDS Res. Hum. Retro.*, 6:1221–1232 [1990].

Reinhardt et al., "Development of viremia and humoral and cellular parameters of immune activation after vaccination with yellow fever virus strain 17d: a model of human flavivirus infection," *J. Med. Virol.*, 56:159–167 [1998].

Rose et al., "An effective AIDS vaccine based on live attenuated vesicular stomatitis virus recombinants," *Cell*, 106:539–549 [2001].

Sambrook et al., *Molecular Cloning: A Laboratory Manual*, Cold Spring Harbor Laboratory, N.Y. [1989].

Sato et al., "Immunostimulatory DNA sequences necessary for effective intradermal gene immunization," *Science*, 273:352–354 [1996].

Schnell, "Viral vectors as potential HIV–1 vaccines," *FEMS Microbiol. Lett.*, 200:123–129 [2001].

Smerdou and Liljestrom, "Two–helper RNA system for production of recombinant Semliki forest virus particles," *J. Virol.*, 73:1092–1098 [1999].

Sukwit et al., "Flow cytometric detection of intracellular cytokines in peripheral blood of HIV–1 infected Thai children," *Asian Pac. J. Allergy Immunol.*, 19:107–113 [2001] abstract only.

Teo et al., "Circular forms of unintegrated human immunodeficiency virus type 1 DNA and high levels of viral protein expression: association with dementia and multinucleated giant cells in the brains of patients with AIDS," *J. Virol.*, 71:2928–2933 [1997].

Van Der Hoek et al., "Genetic differences between human immunodeficiency virus type 1 subpopulations in faeces and serum," *J. Gen. Virol.*, 79:259–267 [1998].

Van Der Loeff et al., "HIV–2 does not protect against HIV–1 infection in a rural community in Guinea–Bissau," *AIDS*, 15:2303–2310 [2001].

Wang et al., "Induction of humoral and cellular immune responses to the human immunodeficiency type 1 virus in nonhuman primates by in vivo DNA inoculation," *Virol.*, 211:102–112 [1995].

Wyand et al., "Vaccine protection by a triple deletion mutant of simian immunodeficiency virus," *J. Virol.*, 70:3724–3733 [1996].

Young, "The replication cycle of HIV–1," Harvard Medical School, HIV InSite Knowledge Base, Chapter 3 [1997].

Huang et al., "Human immunodeficiency virus type 1–specific immunity after genetic immunization is enhanced by modification of Gag and Pol expression," *J. Virol.*, 75:4947–4951 [2001].

Kohler et al., "No hope for an AIDS vaccine soon," *AIDScience*, 2:1–3 [2002].

Moore et al., "Effects of antigen and genetic adjuvants on immune responses to human immunodeficiency virus DNA vaccines in mice," *J. Virol.*, 76:243–250 [2002].

Veljkovic et al., "AIDS epidemic at the beginning of the third millennium: time for a new AIDS vaccine strategy," *Vaccine*, 19:1855–1862 [2001].

* cited by examiner

Artificial
10,791 bp

| Gene | Size | Sequence |
|------|------|----------|
| 5'-LTR |  | 1-634 |
| Gag | p55 | 789-2291 |
| Pol | p160 | 2084-5095 |
| Vif |  | 5040-5618 |
| Vpr |  | 5558-5848 |
| Tat 1 |  | 5829-6032 |
| Rev 1 |  | 5968-6042 |
| Vpu |  | 6060-6302 |

| Gene | Size | Sequence |
|------|------|----------|
| Env | gp160 | 6223-8784 |
|  | gp120 | 6223-7746 |
| RRE |  | 7715-8068 |
|  | gp41 | 7747-8781 |
| Tat 2 |  | 8370-8458 |
| Rev 2 |  | 8370-8642 |
| Nef |  | 8786-9400 |
| 3'-LTR |  | 9078-9713 |

Figure 4

COMPOSITIONS COMPRISING MULTIPLE IMMUNODEFICIENCY VIRUS SUBUNITS FOR INDUCING AN IMMUNE RESPONSE

FIELD OF THE INVENTION

The present invention relates to prophylactic and therapeutic acquired immunodeficiency syndrome vaccines. In particular, the present invention provides methods and compositions utilizing recombinant HIV-1, HIV-2 and/or SIV genes or gene products in safe vaccination approaches.

BACKGROUND OF THE INVENTION

The primary cause of acquired immunodeficiency syndrome (AIDS) is the human immunodeficiency virus (HIV; See, e.g., Levy, 1993, Microbial. Rev. 57:183–289). There are two major HIV groups (HIV-1 and HIV-2) and many subgroups because the HIV genome mutates constantly. The major difference between the groups and subgroups is in the viral envelope. HIV-1 is classified into main subgroup (M) and a $10^{th}$ outlier subgroup (O), in which subgroup M is divided into nine subtypes (clades) designed A through J (Hu et al., 1996, JAMA 275:210–216 and Korber et al., 1998, Science 280:1868–1871). The genetic variation seen in the HIV genome is the result of mutation, recombination, insertion, and deletion (Korber et al., 1998, Science 280:1868–1871). Still further genetic variation has come about as a result of human efforts including the construction of manmade recombinant simian-human immunodeficiency viruses (SHIVs), HIV DNA shuffling, and the inadvertent selection of drug-resistant HIV-1 strains through the use of monotherapy regimens or cocktail therapy. In particular, the mismatch polymerization of HIV reverse transcriptase (RT; van Der Hoek et al., 1998, J. Gen. Virol. 79:259–267) coupled with the high HIV production rate (more than $10^{10}$ virions per day; Perelson et al., 1996, Science 271:1582–1586), has facilitated the rapid generation of sequence variants. These processes in turn result in an extraordinary degree of antigenic variability, which permits subsequent immune evasion.

To date, no HIV vaccine has been shown to protect vaccinated individuals against HIV-1 infection (Mooij and Heeney, 2001, Vaccine, Vol.20:304–21). This is the case even though numerous vaccine modalities including inactivated viral, attenuated live, subunit, peptide, DNA, virus-like particle, pseudovirion, and live recombinant vector (e.g., BCG, vaccinia virus, polio virus, adenovirus, *Salmonella*, etc.) vaccines have been actively explored. Thus, there remains an urgent need in the art for the development of effective methods and compositions for combating immunodeficiency virus infections.

SUMMARY OF THE INVENTION

The present invention relates to prophylactic and therapeutic acquired immunodeficiency syndrome vaccines. In particular, the present invention provides methods and compositions utilizing recombinant HIV-1, HIV-2 and/or SIV genes or gene products in safe vaccination approaches.

The present invention provides methods for administering a vaccine to a subject, comprising the steps of: providing a subject, and at least three subunit vaccines, wherein the vaccines together but not individually comprise a complete immunodeficiency virus genome encoding viral Gag, Pol, Env, regulatory and accessory proteins, in the absence of immunodeficiency virus long terminal repeats; and administering the vaccines to the subject under conditions suitable for inducing an immune response against the viral Gag, Pol, Env, regulatory and accessory proteins. In some embodiments, the subject is selected from the group consisting of an adult, a youth, and a neonate, the subject is a mammal selected from the group consisting of a human, a nonhuman primate, a horse, a cow, a sheep, a rodent, a goat and a cat, and/or the subject is selected from the group consisting of an immunodeficiency virus infected subject and a subject uninfected with an immunodeficiency virus. In further embodiments, the administering is done through at least one route selected from the group consisting of intramuscular, intravenous, intraperitoneal, subcutaneous, oral, intranasal, intravaginal, intrarectal, and stomacheal. In some embodiments, the vaccines are administered in a physiologically acceptable solution. In preferred embodiments, the immune response comprises antibodies reactive with the viral Gag, Pol, Env, regulatory and accessory proteins, the immune response comprises cytotoxic T lymphocytes reactive with the viral Gag, Pol, Env, regulatory and accessory proteins, and/or the immune response comprises helper T lymphocytes reactive with the viral Gag, Pol, Env, regulatory and accessory proteins. In other preferred embodiments, the at least three vaccines comprise a first vaccine, a second vaccine, and a third vaccine, and wherein the second vaccine is administered after the first vaccine has induced an immune response, and the third vaccine is administered after the second vaccine has induced an immune response.

Additionally, the present invention provides methods for producing a set of at least three subunit vaccines comprising the steps of: cloning genes of at least one immunodeficiency virus; mutating at least one of the genes; constructing a library by ligating the genes individually or in combination into at least one vector; and classifying members of the library into a set of at least three subunit vaccines, wherein the vaccines together but not individually comprise a complete immunodeficiency virus genome encoding viral Gag, Pol, Env, regulatory and accessory proteins, in the absence of immunodeficiency virus long terminal repeats. In preferred embodiments, the immunodeficiency virus is selected from the group consisting of HIV-1, HIV-2, SIV, and SHIV. In other preferred embodiments, the at least one immunodeficiency virus genome further comprises at least one gene derived from a distinct immunodeficiency virus. In further embodiments, the at least one vector is selected derived from the group consisting of a plasmid vector, an artificial chromosome vector, a bacterial vector, a fungal vector, and a viral vector. Also provided are embodiments, wherein the mutating comprises introduction of at least one mutation into the active site of a viral Pol protein selected from the group consisting of protease, reverse transcriptase, RNase H and integrase. In other embodiments, at least one of the subunit vaccines further comprises a pharmaceutically suitable carrier. Also provided are embodiments, wherein at least one of the subunit vaccines further comprise at least one molecular adjuvant selected from the group consisting of a co-stimulatory molecule, a cytokine, a chemokine and a growth factor. In still further preferred embodiments, the set of at least three subunit vaccines is suitable for production of a pseudoviral particle comprising structural, regulatory and accessory proteins from the immunodeficiency virus. In related embodiments, the pseudoviral particle comprises the immunodeficiency virus gag gene in the absence of the immunodeficiency virus env gene. In other related embodiments, the pseudoviral particle is incapable of producing viral progeny.

Also provided by the present invention are compositions comprising at least three subunit vaccines, wherein the subunit vaccines together but not individually comprise a complete immunodeficiency virus genome encoding viral Gag, Pol, Env, regulator and accessory proteins, in the absence of immunodeficiency virus long terminal repeats. In preferred embodiments, the immunodeficiency virus is selected from the group consisting of HIV-1, HIV-2, SIV, and SHIV. In other preferred embodiments, the at least one immunodeficiency virus genome further comprises at least one gene derived from a distinct immunodeficiency virus. In some embodiments, the at least three subunit vaccines comprise at least one vector selected from the group consisting of a plasmid vector, an artificial chromosome vector, a bacterial vector, a fungal vector, and a viral vector. In some preferred embodiments, at least one of the viral Pol proteins bears a mutation in its active site. In other embodiments, at least one of the subunit vaccines further comprise a pharmaceutically suitable carrier. Also provided are embodiments, wherein at least one of the subunit vaccines further comprise at least one molecular adjuvant selected from the group consisting of a co-stimulatory molecule, a cytokine, a chemokine and a growth factor. In further preferred embodiments, the at least three subunit vaccines are suitable for production of a pseudoviral particle comprising structural, regulatory and accessory proteins from the immunodeficiency virus. In related embodiments, the pseudoviral particle comprises the immunodeficiency virus gag gene in the absence of the immunodeficiency virus env gene. In other related embodiments, the pseudoviral particle is incapable of producing viral progeny.

DESCRIPTION OF THE FIGURES

The following figures form part of the specification and are included to further demonstrate certain aspects and embodiments of the present invention. The invention may be better understood by reference to one or more of these figures in combination with the detailed description of specific embodiments presented herein.

FIG. 1 provides a schematic of the linear HIV-1 proviral genome, with coding sequences of the HIV-1 genes depicted as open rectangles.

FIG. 2 provides a listing of the HIV-1 genes of an artificial gene construct.

FIG. 3 provides a representative sampling of the HIV-1 genes included in various subunit vaccines.

FIG. 4 provides a schematic of one embodiment of the vaccination method of the present invention comprising five subunit vaccines.

FIG. 5 provides a schematic of two subunit vaccine groups suitable for the production of suicidal HIV-1 pseudoviral particles in vitro.

DEFINITIONS

To facilitate understanding of the invention, a number of terms are defined below.

The term "vaccine" as used herein, refers to a composition that is administered to produce or artificially increase immunity to a particular disease. For example, "vaccine compositions" frequently comprise a preparation of killed or live attenuated microorganisms. Alternatively, subunit vaccines frequently comprise a preparation of isolated nucleic acids or proteins corresponding to the genes or gene products of a microorganism of interest.

The term "subunit vaccine" as used herein refers to a vaccine composition that comprises either purified antigenic determinants or nucleic acids encoding the purified antigenic determinants, in the absence of the disease-causing organism. In some embodiments of the present invention, the nucleic acids are part of a plasmid, an artificial chromosome or a heterologous recombinant organism.

As used herein, the term "preventive vaccine" refers to a vaccine composition suitable for administration to uninfected subjects and which in preferred embodiments provides protection from microbial (e.g., viral) infection or in other embodiments reduces the severity of the microbial invention (e.g., reduced viral load). The term "therapeutic vaccine" refers to a vaccine composition suitable for administration to infected subjects and which in preferred embodiments prevents or delays disease.

The term "subject" as used herein, refers to any animal (e.g., a mammal), including, but not limited to, humans, non-human primates, rodents, ovines, bovines, ruminants, lagomorphs, porcines, caprines, equines, canines, felines, aves, etc. Typically, the terms "subject" and "patient" are used interchangeably in reference to a human subject.

As used herein the term "mammal" refers to animals of the class Mammalia, including warm-blooded higher vertebrates such as placentals, marsupials, or monotremes, that nourish their young with milk secreted by mammary glands.

The term "at least" as used herein, refers to the minimum number or quantity suitable for various embodiments of the present invention. For instance, "at least four subunit vaccines" refers to four or more subunit vaccines.

The phrase "vaccines together but not individually comprise a complete immunodeficiency virus genome" as used herein, refers to a vaccine group in which the aggregate, but not each separate vaccine in the group comprises a complete genome.

The term "immunodeficiency virus" refers to any lentivirus or to any member of the Lentivirus family, which is capable of causing immune suppression in an infected animal. In some embodiments, the term "immunodeficiency virus" refers to the retrovirus known as the human immunodeficiency virus (HIV), which is responsible for the fatal illness termed the acquired immunodeficiency syndrome (AIDS). Two kinds of HIV have been identified: HIV-1 is the more virulent, pandemic virus, and HIV-2 is the closely related virus largely confined to West Africa. The term "immunodeficiency virus" also refers to viruses causing immune suppression in nonhuman animals, and including but not limited to SIV (primates), BIV and JDV (cattle), FIV (cats), MVV (sheep), OLV (sheep and goats), CAEV (goats), and EIAV (horses).

As used herein, the term "genome" refers to the total set of genes carried by an organism. In preferred embodiments, the term "genome" refers to the complete set of genes from an immunodeficiency virus. The term "gene" refers to a specific sequence of nucleotides (e.g., DNA or RNA) that is the functional unit of inheritance controlling the transmission and expression of one or more traits.

The terms "Gag" and "group specific antigen" refer to the immunodeficiency virus polyprotein composed of MA, CA, NC, and p6.

The terms "Pol" and "polymerase" refer to the immunodeficiency virus polyprotein composed of the protease, reverse transcriptase, RNaseH and integrase enzymes.

The terms "Env" and "envelope" refer to the immunodeficiency virus polyprotein (e.g., gp160) composed of surface (e.g., gp120) and transmembrane (e.g., gp41) subunits.

As used herein, the term "regulatory protein" refers to the small immunodeficiency virus proteins involved in modulation of the viral replicative cycle, including Tat, and Rev.

As used herein, the term "accessory protein" refers to the small immunodeficiency virus proteins whose functions have been shown to be dispensable in vitro, including but not limited to Nef, Vpu, Vpr, and Vif.

The term "suitable for" as used herein, refers to a condition or a combination adapted to a specific use or purpose. In some embodiments, "suitable for" refers to conditions for administration of a vaccine to a subject; as such this term encompasses but is not limited to an appropriate vaccine dosage (e.g., less than 10 cc), an appropriate vaccine formulation (e.g., alum adjuvant), and an appropriate vaccine schedule (See, e.g., Tables 1 and 2). In other embodiments, "suitable for" refers to a particular combination of vaccines appropriate for production of a suicidal pseudoviral particle.

As used herein, the term "immune response" refers to the alteration in the reactivity of an organism's immune system upon exposure to an antigen. The term "immune response" encompasses but is not limited to one or both of the following responses: antibody production (e.g., humoral immunity), and induction of cell-mediated immunity (e.g., cellular immunity including helper T cell and/or cytotoxic T cell responses).

The term "adult" refers to adolescent and mature subjects. The term "youth" refers to immature subjects (e.g., children). The term "neonate" refers to newborn subjects (e.g., babies).

The term "route" as used herein, refers to methods for administration of a prophylactic or therapeutic agent. In some embodiments, "route" refers to the method of administration of a vaccine including but not limited to intramuscular, intravenous, intraperitoneal, subcutaneous, oral, intranasal, intravaginal, intrarectal, and stomacheal administration methods.

As used herein, the term "physiologically acceptable solution" refers to an isotonic solution such as an aqueous solution comprising for example, saline, phosphate buffered saline, Hanks' solution, or Ringer's solution.

The term "infected" as used herein, refers to a subject in which a pathogen has established itself. In preferred embodiments, the term "infected subject" refers to a subject that is infected with an immunodeficiency virus. In contrast, the term "uninfected" refers to a subject which has not been contaminated with a pathogen. In preferred embodiments, the term "uninfected subject" refers to a subject that is not infected with an immunodeficiency virus. In the context of the invention, the term "uninfected subject" encompasses subjects which may be infected with other types of viruses (e.g., CMV, EBV, etc.).

The term "control" refers to subjects or samples which provide a basis for comparison for experimental subjects or samples. For instance, the use of control subjects or samples permits determinations to be made regarding the efficacy of experimental procedures. In some embodiments, the term "control subject" refers to animals which receive a mock treatment (e.g., empty vector).

As used herein, the term "antibodies reactive with" refers to antibodies which bind to or react with an antigen of interest. In preferred embodiments of the present invention, the term "antibodies reactive with" is used in reference to antibodies which bind to the immunodeficiency virus of interest, or viral Gag, Pol, Env, regulatory or accessory proteins.

The term "cytotoxic T lymphocytes reactive with" refers to cytotoxic T lymphocytes capable of lysing an MHC (e.g., HLA)-matched cell presenting epitopes derived from an antigen of interest. In preferred embodiments of the present invention, the term "cytotoxic T lymphocytes reactive with" is used in reference to cytotoxic T lymphocytes or CTLs capable of lysing a MHC-matched cell infected by the immunodeficiency virus of interest, or presenting epitopes derived from viral Gag, Pol, Env, regulatory or accessory proteins.

The term "helper T lymphocytes reactive with" refers to helper T lymphocytes capable of secreting lymphokines in response to an MHC (e.g., HLA)-matched cell presenting epitopes derived from an antigen of interest. In preferred embodiments of the present invention, the term "helper T lymphocytes reactive with" is used in reference to helper T lymphocytes or $T_H$ cells capable of secreting lymphokines in response to an MHC-matched cell infected by the immunodeficiency virus of interest, or presenting epitopes derived from viral Gag, Pol, Env, regulatory or accessory proteins.

As used herein, the term "induced an immune response" refers to an immune response elicited by a vaccine or a set of vaccines of the present invention.

The term "cloning" refers to the use of nucleic acid manipulation procedures to produce multiple copies of a single gene or gene fragment of interest.

As used herein, the term "mutating" refers to the use of one of a number of procedures (e.g., site-directed mutagenesis, chemical, etc.) for altering a nucleic acid sequence. In preferred embodiments, the term "mutating" refers to the use of molecular techniques for introducing deleterious changes to an immunodeficiency virus gene. Deleterious changes include but are not limited to premature stop codons in a viral gene and substitutions which destroy viral enzymatic activity.

"Wild-type," as used herein, refers to a gene or gene product which has the characteristics of that gene or gene product when isolated from a naturally occurring source. A wild-type gene is that which is most frequently observed in a population and is thus arbitrarily designed the "normal" or "wild-type" form of the gene.

"Mutant," as used herein, refers to any changes made to a wild-type nucleotide sequence, either naturally or artificially, that produces a translation product that functions with enhanced or decreased efficiency in at least one of a number of ways including, but not limited to, specificity for various interactive molecules, rate of reaction and longevity of the mutant molecule.

The term "ligating" refers to the process of joining nucleic acid fragments together.

As used herein, the term "classifying" refers to the categorization of vaccines into desired groups.

As used herein, the term "virulent" refers to markedly pathogenic immunodeficiency viruses (e.g., viruses capable of causing severe disease).

The term "distinct" refers to immunodeficiency viruses which are distinguishable from one another (e.g., different strain, different clade, different tropism, etc.).

As used herein, the term "vector" refers to a system used to transfer nucleic acid sequences from one cell to another or from one organism to another. Appropriate vectors for making and using the vaccines of the present invention include but are not limited to plasmids (e.g., pcDNA3.1), artificial chromosomes, bacteria, fungi, and viruses (e.g., vaccinia virus, adeno-associated virus, poliovirus, etc.).

The terms "expression vector," "expression construct," "expression cassette" and "plasmid," as used herein refer to a recombinant nucleic acid molecule containing a desired coding sequence and appropriate nucleic acid sequences necessary for the expression of the operably linked coding sequence in a particular host organism. The sequences may be either double or single-stranded. Nucleic acid sequences necessary for expression in prokaryotes usually include a promoter, an operator (optional), and a ribosome-binding site, often along with other sequences. Eukaryotic cells are known to utilize promoters, enhancers, and termination and polyadenylation signals.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The terms also refer to the linkage of amino acid sequences in such a manner so that a functional protein is produced.

As used herein, the term "strain" refers to a group of presumed common ancestry, but with some clear-cut genetic distinctions (e.g., not clones). In preferred embodiments, the term "strain" is used in reference to distinct immunodeficiency virus isolates.

The terms "human immunodeficiency virus type-1" and "HIV-1" refer to the lentivirus which is widely recognized as the aetiologic agent of the acquired immunodeficiency syndrome (AIDS). HIV-1 is characterized by its cytopathic effect and affinity for CD4+-lymphocytes and macrophages. The terms "human immunodeficiency virus type-2" and "HIV-2" refer to a lentivirus related to HIV-1 but carrying different antigenic components and with differing nucleic acid composition. The term "recombinant HIV strain" refers to an HIV virus produced from an immunodeficiency virus genome that has been assembled through the use of molecular biology techniques that are well known in the art. The terms "simian immunodeficiency virus" and "SIV" refer to lentiviruses related to HIV, which cause acquired immunodeficiency syndrome in nonhuman primates (e.g., monkeys and apes). The terms "simian human immunodeficiency virus" and "SHIV" refer to various man-made chimeric retroviruses having both human and monkey immunodeficiency virus genes. The terms "feline immunodeficiency virus" and "FIV" refer to lentiviruses which cause acquired immunodeficiency syndrome in cats (e.g., cats and lions). The terms "bovine immunodeficiency virus" and "BIV" refer to lentiviruses which cause acquired immunodeficiency syndrome in cattle. Similarly, the terms "Jembrana disease virus" and "JDV" refer to lentiviruses distinct from BIV, but which also cause acquired immunodeficiency syndrome in cattle. The terms "equine infectious anemia virus" and "EIAV" refer to lentiviruses which cause acquired immunodeficiency syndrome in horses. The terms "caprine arthritis-encephalitis virus" and "CAEV" refer to lentiviruses which cause acquired immunodeficiency syndrome in goats. The terms "maedi-visna virus," "visna virus" and "MVV" refer to lentiviruses which cause acquired immunodeficiency syndrome in sheep. The terms "ovine lentivirus" and "OLV" refer to lentiviruses which cause acquired immunodeficiency syndrome in goats and sheep.

As used herein, the term "mutation" refers to a permanent transmissible change in genetic material encompassing but not limited to substitutions, deletions, and insertions.

The term "active site" refers to a specific region of an enzyme where a substrate binds (binding site) and catalysis (catalytic site) takes place.

As used herein, the term "viral enzyme" refers to viral proteins which catalyze chemical reactions of other substances without being destroyed or altered upon completion of the reactions. The terms "protease" and "Pro" refer to a viral enzyme that catalyses the splitting of interior peptide bonds in a protein. The terms "reverse transcriptase" and "RT" refer to a viral enzyme involved in the synthesis of double stranded DNA molecules from the single stranded RNA templates. The terms "RNase H" and "Ribonuclease H" refer to a viral enzyme which specifically cleaves an RNA base paired to a complementary DNA strand. The terms "integrase" and "IN" refer to a viral enzyme which inserts a viral genome into a host chromosome.

As used herein, the terms "long terminal repeat" and "LTR" refer to homologous nucleic acid sequences, several hundred nucleotides long, found at either end of a proviral DNA, and formed by reverse transcription of retroviral RNA. LTRs are thought to have an essential role in integrating the provirus into the host DNA. In proviruses the upstream LTR acts as a promoter and enhancer and the downstream LTR acts as a polyadenylation site.

The term "adjuvant" refers to a substance added to a vaccine to improve the immune response (e.g., alum). As used herein, the term "molecular adjuvant" refers to proteins which improve the immunogenicity of a vaccine or to the genes which encode these proteins. The term "molecular adjuvant" encompasses but is not limited to costimulatory molecules, cytokines, chemokines, growth factors, etc.

As used herein, the term "costimulatory molecule" refers to a molecule on the surface of or secreted by an antigen presenting cell which provides a stimulus or second signal required for activation of T cells. The term "costimulatory molecule" encompasses but is not limited to B7-1 and B7-2 (CD80 and CD86).

The term "cytokine" refers to small proteins or biological factors (in the range of 5–20 kD) that are released by cells and which have specific effects on cell-cell interaction, communication and behavior of other cells. The term cytokine encompasses but is not limited to interleukins and lymphokines.

The term "chemokine" refers to cytokines that are chemotactic for leucocytes. They are subdivided into two groups on the basis of the arrangement of a pair of conserved cysteines. The CXC group of chemokines have paired cysteines separated by a different amino acid, and are chemoattractants for neutrophils but not monocytes. The CC group of chemokines have adjacent cysteines, and are chemoattractants for lymphocytes, monocytes, eosinophils, basophils but not neutrophils. The term "chemokine" encompasses but is not limited to platelet factor-4, platelet basic protein, interleukin-8, melanoma growth stimulatory protein, and macrophage inflammatory protein 2.

The term "growth factor" refers to biological factors that are produced by the body to control growth, division and maturation of cells. "Growth factors" include but are not limited to epidermal growth factor, platelet-derived growth factor, fibroblast growth factor, etc.

The terms "pseudovirus," "pseudoviral particle" and "virus-like particle" refer to self-assembling, non-replicating, virus-sized structures that closely resemble an intact virion. However, since pseudoviral particles do not contain a complete viral genome, they are incapable of replication and their infection is suicidal, thus "pseudoviral particles" are also called "suicide particles" or "suicidal particles."

The term "transfection" as used herein refers to the introduction of foreign nucleic acid (e.g., DNA) into cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, biolistics (i.e., particle bombardment), and the like.

As used herein, the term "polymerase chain reaction" ("PCR") refers to the method of K. B. Mullis U.S. Pat. Nos. 4,683,195, 4,683,202, and 4,965,188, hereby incorporated by reference, that describe a method for increasing the concentration of a segment of a target sequence in a DNA mixture without cloning or purification. Because the desired amplified segments of the target sequence become the predominant sequences (in terms of concentration) in the mixture, they are said to be "PCR amplified." Similarly, the term "modified PCR" as used herein refers to amplification methods in which a RNA sequence is amplified from a DNA template in the presence of RNA polymerase or in which a DNA sequence is amplified from an RNA template the presence of reverse transcriptase.

DESCRIPTION OF THE INVENTION

The present invention relates to prophylactic and therapeutic acquired immunodeficiency syndrome vaccines. In particular, the present invention provides methods and compositions utilizing recombinant HIV-1, HIV-2 and/or SIV genes or gene products in safe vaccination approaches.

Figure 1:
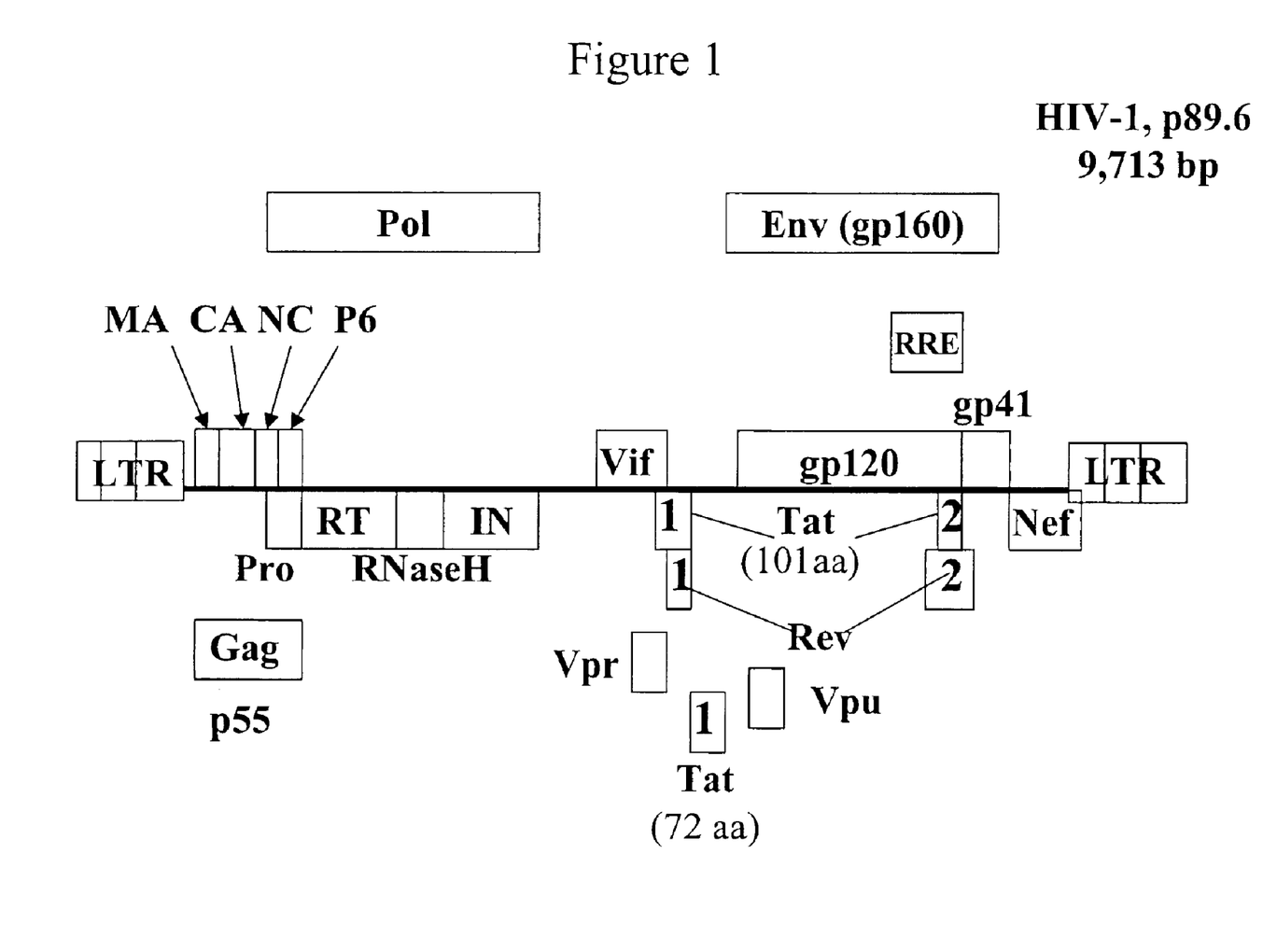

HIV is a single-stranded RNA virus of about 9.7 kilobases (Muesing et al., 1985, Nature 313:450–458). The double stranded DNA form of HIV is known as the provirus. The HIV provirus can exist as an integrated linear form with both ends flanked by the long terminal repeats (LTRs; Gallo et al., 1988, Nature 333:504.), or as an unintegrated circular form with one or two LTRs (Pang et al., 1990, Nature 343:85–89; and Teo et al., 1997, J. Virol. 71:2928–2933). The central genes of the proviral DNA encode more than nine proteins that are classified as major structural proteins (Gag, Pol, and Env); regulatory proteins (Tat and Rev); and accessory proteins (Vpu, Vpr, Vif, and Nef; Emerman and Malim, 1998, Science 280:1880–1884). As can be seen in the schematic of the HIV-1 genome provided in FIG. 1, some of these proteins can be cleaved into smaller functional proteins or enzymes during the process of viral maturation. For example, the 55-kilodalton (kD) Gag precursor protein is cleaved into four smaller proteins designated MA (matrix or p17), CA (capsid or p24), NC (nucleocapsid or p9), and p6; while 160 kD Env (gp160) is cleaved into gp41 and gp120 (Gottlinger et al., 1989, Proc. Natl. Acad. Sci. USA, 86:5781–5785; Jacks et al., 1988, Nature 331:280–283; and Bernstein et al., 1995, J. Virol. 69:2745–275).

The present invention provides multiple vaccines each containing a portion of the HIV genome, such that a complete set of vaccines encompasses most of the HIV genome, with the exception of the viral LTRs. Importantly, the vaccines and vaccination regimens of the present invention elicit an immune response in vaccinated individuals without risk of HIV infection. Thus, the present invention is contemplated to prevent and treat AIDS. Any live vectors or plasmids, and any genes or gene fragments obtained from HIV, are suitable for use with the present invention as a means to generate recombinant vaccines. The vaccines of the present invention can be administered to subjects sequentially or in combination. Additionally, the disclosed methods are suitable for use in generating AIDS vaccines for nonhuman animals, such as bovine immunodeficiency virus and feline immunodeficiency virus vaccines and vaccination regimens, for prevention and treatment of AIDS in cows and cats, respectively.

Figure 2:
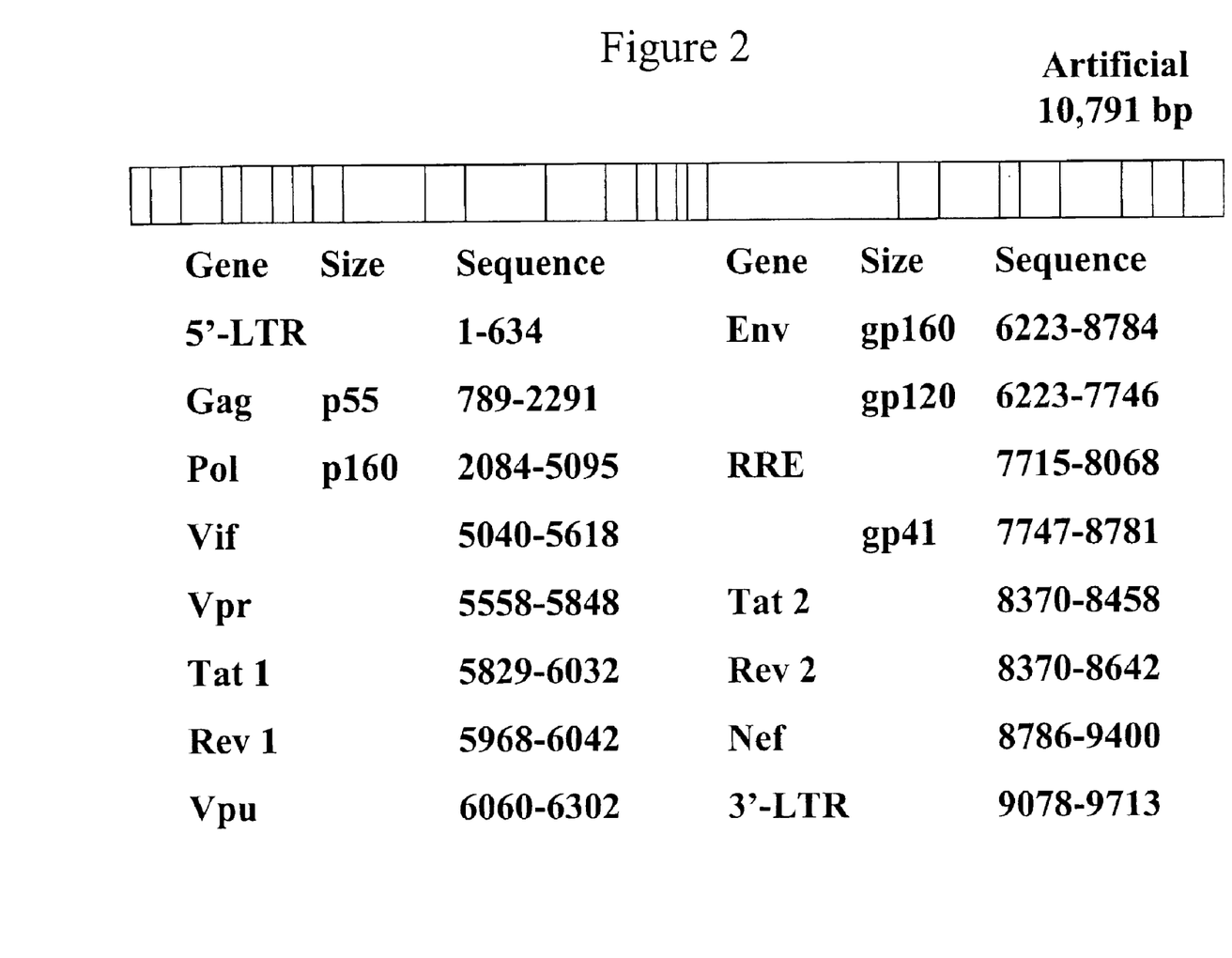
Figure 3:
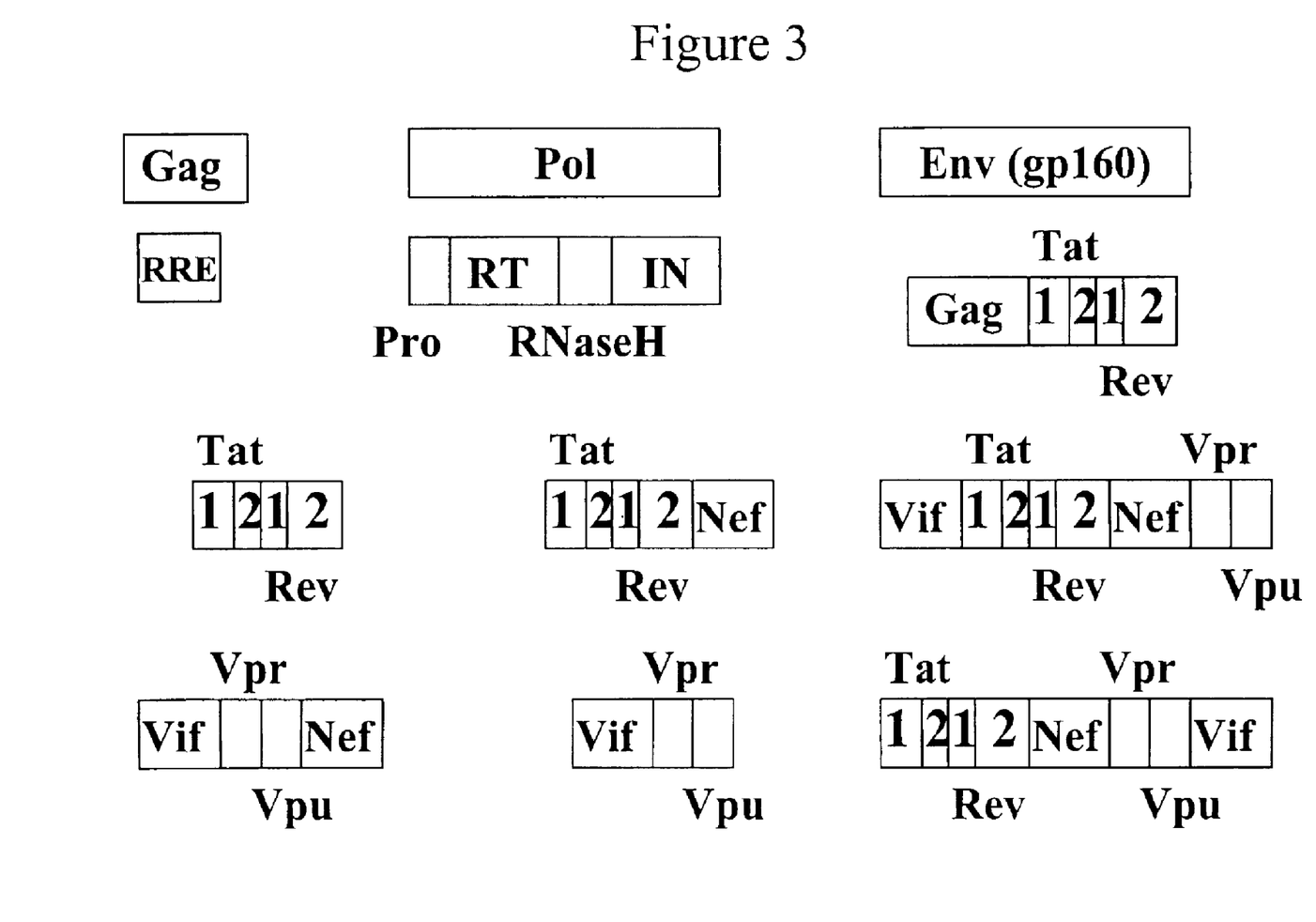

A method, in one of the embodiments of the present invention, for producing vaccines comprises: fragmenting the HIV-1 proviral genome into fragments containing functional genes, some genes contain contiguous sequences (See, FIG. 2); mutating the HIV-1 replicon genes such that the expressed proteins are structurally similar, but enzymatically nonfunctional; inserting the HIV-1 fragments into expression vectors such that the fragments can be transcribed and translated to form viral proteins in vivo or in vitro (See, FIG. 3). In some embodiments, the expression vectors are suitable for the production of pseudoviral virions (e.g., suicidal HIV-1 particles, See, FIG. 5).

Testing of the vaccination regimens of the present invention is contemplated to be done in nonhuman primates or cats and comprises: inoculating subjects with the AIDS vaccines sequentially and/or in combination; evaluating the immune responses elicited by the AIDS vaccines before a subsequent inoculation; and challenging the subjects with lethal viral strains upon completion of the vaccine regimen, to test the safety and efficacy of the vaccines.

Specifically, all of the genomic fragments obtained from an HIV provirus, with the exception of the LTRs, are cloned into live vectors or plasmids to generate subunit vaccines. One fragment containing one gene or several genes, or several smaller fragments containing single genes corresponding to those of the larger fragment are grouped together. For example, a chimeric gene fragment containing vpu-vpr-vif-nef cloned into an adenoviral vector, and vpu, vpr, vif, and nef genes cloned individually into an adenoviral vector are grouped together. In a preferred embodiment, the first group of vaccines (Vaccine Group I) are administered to subjects by intramuscular (IM) injection. However, other routes of inoculation, including but not limited to, intranasal (IN), oral (PO), intravaginal (IVG), intravenous (IV) or intrarectal (IR), are also suitable. The second vaccination, using the second group of vaccines (Vaccine Group II), is administered after the first group has elicited an immune response. The third vaccination, using the third group of vaccines (Vaccine Group III), is administered after Vaccine Groups I and II have elicited immune responses. The vaccination methods of the present invention may further include repetition of these steps with a fourth or more vaccine(s). Thus, numerous successive rounds of vaccination may be appropriate for use with the present invention. Additionally, purified viral proteins and/or cytokines may be used to boost the immune responses elicited by vaccination. However, fewer vaccination rounds are necessary when vaccines from multiple groups are administered simultaneously.

The present invention is discussed in more detail below, and is exemplified herein using $SIV_{mac251}$ and the pCR3.1 plasmid in the rhesus macaque model. However, the present invention is not limited to this virus, vector and/or animal model, which are provided merely as illustrations. Analogous procedures and techniques are equally applicable to: other RNA viruses (e.g., $HIV-1_{89.6}$, $HIV-1_{YU-2}$, $SIV_{mac239}$, $HIV-2_{ROD}$, $FIV_{petaluma}$/FPBM, etc.); other vectors (e.g., SFV, YFV 17D vector, AAV vector, BCG vector, pcDNA3.1 (+/−), pCEFL, etc.); and other subjects (e.g., African green monkeys, chimpanzees, humans, cats, etc.).

Selection of HIV/SIV Genes for AIDS Vaccines

The main barriers to the development of effective HIV vaccines as exemplified by the failure of attenuated and inactivated viral vaccines are: inadequate virus attenuation or inactivation; extensive viral sequence variation; viral integration into the host genome leading to latent infection; and viral transmission by both virions and virus-infected cells.

Figure 4:
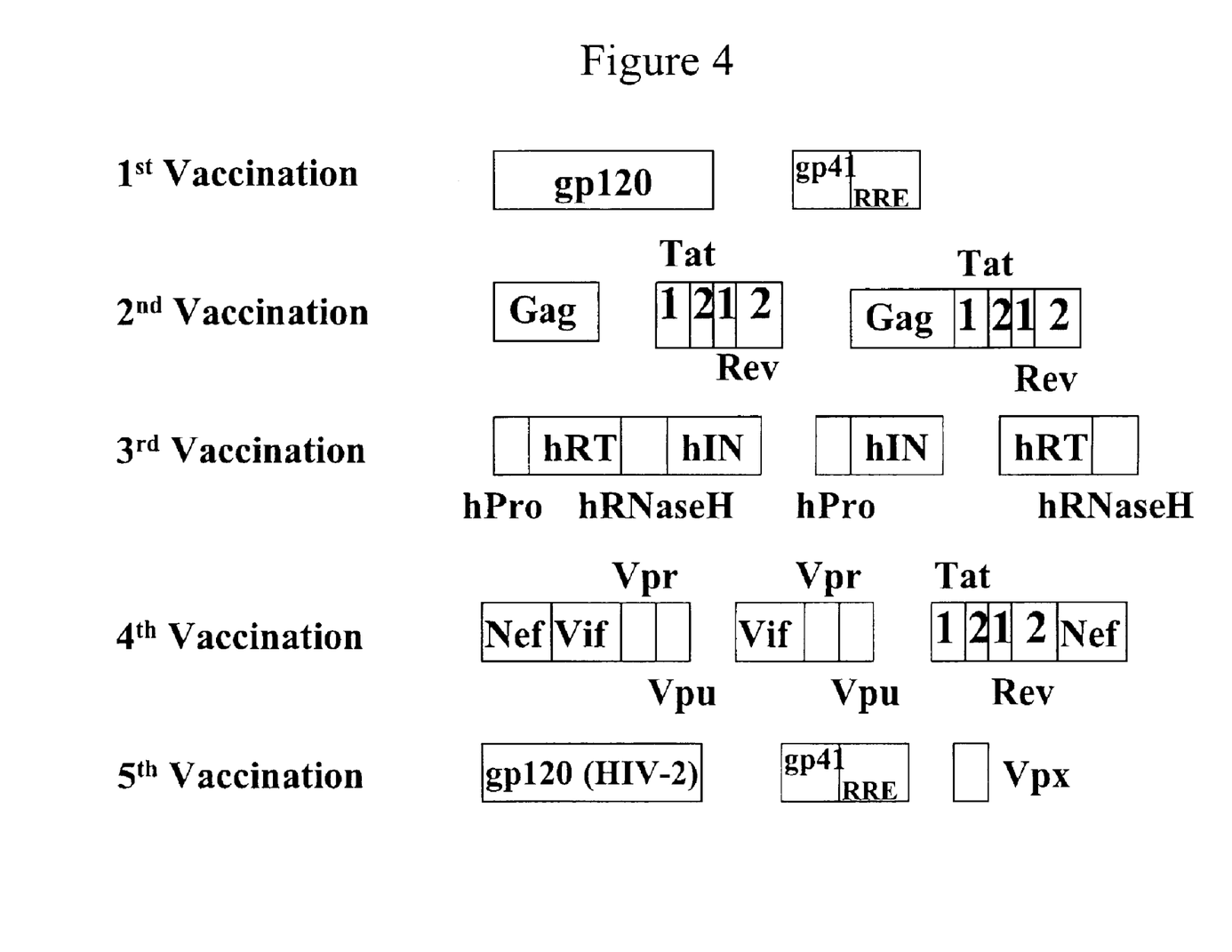

To overcome these barriers to the generation of effective AIDS vaccines, the viral clade and viral genes used in the vaccines of the present invention are carefully selected. In preferred embodiments, the sequence of an infectious HIV or SIV viral isolate (e.g., $SIV_{mac251}$, $HIV-1_{89\ 6}$, $HIV-2_{ROD}$, etc.) is used. For illustration purposes, one embodiment of the vaccination regimen of the present invention is shown in FIG. 4. A second embodiment is described in more detail below:

1. gag fragment for construction of Vaccine Group I;
2. vif to rev fragment, including vif, vpr, vpu (vpx in SIV), plus nef and tat genes for construction of Vaccine Group II;
3. pol and gpp fragment for construction of Vaccine Group III;
4. env fragment for construction of Vaccine Group IV;
5. gag, pol, and env fragments from a second HIV clade for construction of Vaccine Group V;
6. 5'-LTR, and 3'-LTR for construction of Vaccine Group VI; and
7. pseudoviral particles produced from the genes of Vaccine Groups I-IV constitute Vaccine Group VII.

All pol genes or genes from pol, including Pro, RT, IN, and Rnase H genes, are used as either wild type or mutated forms. The gene arrangement and gene order used in vaccine constructs of the present invention may differ from the specific embodiments disclosed herein. For instance, an AIDS vaccine may include a single construct or vector containing tat, rev, nef, vif, vpr, and vpu genes in any order, or it may include a first construct containing the tat and rev genes, and a second construct containing nef, vif, vpr, and vpu genes. Alternatively, an AIDS vaccine may comprise multiple constructs each containing a single gene. The HIV tat gene may be constructed in such a way that two tat genes, an early fully spliced tat gene and a late incompletely spliced tat gene, are cloned side-by-side with other genes. Additionally, HIV genes with loss of function mutations may be included in constructs that are contemplated to be within the scope of the present invention. Regardless of the order in which they are administered, a complete set of vaccines of the present invention encompasses at least one viral genome of a particular virus, in the absence of the viral LTRs (which are included only as controls in Vaccine Group VI above). In some embodiments, the vaccines of the present invention may include genes from a distinct immunodeficiency virus or strain (e.g., HIV-2 gag, pol, and/or env). Importantly, the vaccines of the present invention encompass the entire HIV genome in the absence of the LTRs, and the full set of vaccines approximate the composition of an inactivated or attenuated viral vaccine. The pseudovirus particles of the present invention produced by the packaging of the virus genes of Vaccine Groups I to IV, are contemplated to yield immunogenic, suicidal viral particle incapable of reproducing viral progeny. When the vaccines of the present invention include genes from multiple viruses or strains (e.g., HIV-1 pol and HIV-2 pol), a broader immune response may be obtained. Furthermore, since any given member of the vaccine group does not contain a complete viral genome, the risk of vaccine-caused infection is negligible. Repeated vaccinations should boost the subject's immune response to a level adequate for preventing HIV infection.

The genes used in the vaccines of the present invention can be selected from any immunodeficiency viruses, including but not limited to primate viruses (e.g., HIV-1, HIV-2, SIV, SHIV) and nonhuman animal viruses such as BIV or JDV (cattle), FIV (cat), MVV or OLV (sheep), CAEV or OLV (goat), and EIAV (horse). If not specifically identified, HIV encompasses all subtypes of either HIV-1 or HIV-2. HIV-1 encompasses all subtypes of HIV-1. HIV-2 encompasses all subtypes of HIV-2. SIV encompasses all subtypes of SIV and SHIV. SHIV encompasses all subtypes of SHIV. BIV encompasses all subtypes of BIV. FIV encompasses all subtypes of FIV, etc.

Construction of AIDS Vaccines

For illustration purpose only, AIDS vaccines are constructed from proviral DNA cloned in constructs containing partial or nearly complete HIV/SIV sequences. HIV/SIV DNA is either treated with restriction enzymes or PCR amplified to produce fragments of the desired size. Computer programs can be utilized to select the appropriate restriction sites or PCR primer sites within the HIV/SIV sequence. Alternatively, restriction sites or PCR primer sites located on the multiple cloning site of the HIV/SIV constructs can be utilized. If particular sequences of interest have no existing restriction sites, specific oligo-primers are designed for use in PCR, to generate viral DNA fragments containing the sites of interest. Additionally, point and cassette mutations, start and stop codon insertion, gene fusion, gene recombination and rearrangement, are employed as necessary to generate the fragments of interest. The desired fragments are then size-fractionated and purified by for example, agarose gel electrophoresis. Purified fragments are ligated into appropriate expression vectors or plasmids. In preferred embodiments a viral based live vector or a plasmid are utilized. In some embodiments, all vaccine groups are constructed from a single vector. However, it is not necessary for the vaccines to be constructed from a single vector. For instance, Vaccine Group I may include a viral vector such as Semliki forest virus vector or adeno-associated virus vector, while Vaccine Group II may include a plasmid such as pCR3.1, and Vaccine Group III may include a bacterial vector such as BCG. However, the use of the same vector may reduce the vaccinated subjects' immune response to the HIV gene product. For example, a subject who has been previously exposed to vaccinia virus may require a higher vaccine titer in order to induce an immune response to of the same magnitude as that elicited by vaccinia virus administered to a naive subject.

Expression vectors that are derived from viruses (e.g., Semliki forest virus, poliovirus, adeno-associated virus, murine leukemia virus, Moloney murine leukemia virus, influenza virus, yellow fever virus, etc), microorganisms (e.g., *bacille calmette gurin, Salmonella typhimurium, Listeria monocytogenes*, etc.), or plasmids (e.g., pCR3.1, pcDNA3.1, pCEFL, etc.), are suitable for use in construction of the vaccines of the present invention. Well-established methods are used to construct recombinant AIDS vaccines containing HIV/SIV genes in operable combination with promoters to control HIV/SIV gene expression (Ausubel et al., 1989, Current Protocols in Molecular Biology, Greene Publishing Associates and Wiley Interscience, N.Y.; and Sambrook et al., 1989, Molecular Cloning: A Laboratory Manual. Cold Spring Harbor Laboratory, NY). In cases where a yellow fever virus is used as an expression vector, an HIV/SIV sequence may be incorporated into the capsid and nonstructural genes of the yellow fever (17D) virus isolate to produce a viable recombinant yellow fever virus capable of expressing HIV genes and proteins in inoculated subjects (Monath et al., 1999, Vaccine 17:1869–1882; and Galler et al., 1997, Brazilian J. Med. Biol. Res. 30:157–168).

Alternatively, HIV/SIV genes or recombinant HIV/SIV genes can be reconstituted into liposomes or other vaccine packaging agents for delivery to target cells or subjects. All molecules that are present in a vaccine packaging agent at the time of vaccine formation (e.g., naked plasmid DNA) are incorporated into the vaccine to protect the vaccine contents from the external environment or to control the release of the vaccine contents over time.

Special initiation signals may also be required for efficient translation of inserted HIV/SIV sequences. Exogenous transcriptional control signals, including an ATG initiation codon, may be provided. Furthermore, initiation codons must be in phase with the viral reading frame to ensure proper translation. These exogenous translational control signals and initiation codons can be of either natural or synthetic origin. In addition, the efficiency of expression may be enhanced by the inclusion of appropriate transcription enhancer elements, a promoter, transcription terminators, etc. (Bitterner et al., 1987, Methods in Enzymol. 153:516–544; and Sato et al., 1996, Science, 273:352–354).

The present invention also encompasses modifications of the HIV/SIV fragments such as epitope or green fluorescent protein tags, in order to more easily monitor the HIV/SIV gene products. Some protease cleavage sites may be introduced between genes in order to generate appropriate proteins. The vaccines may be administered in adjuvants or pharmaceutically-acceptable diluents when appropriate.

When viral vectors are used, the recombinant vaccine candidates are first transfected into a packaging cell line to produce viral particles. For plasmid vaccine candidates, any *Escherichia coli* stain (e.g., DH5α or Top 10) can be used to produce plasmids and/or to express proteins. In a preferred method, human cells or animal cells are used. In some embodiments, the recombinant vaccine contains a selectable marker permitting the selective growth of cells containing the recombinant vaccine, or that allows selective production of plasmid containing an insert. Prior to administration, all inserts will be sequenced to confirm their identity.

Vaccination Regimens

The AIDS vaccines of the present invention may be used both prophylactically and therapeutically. In preferred embodiments, the AIDS vaccines elicit both humoral and cellular immune responses.

Common Vector Method

The AIDS vaccines used in the common vector method include a vaccine set containing different inserts within a common vector (e.g., pCR3.1). Subjects are first given a set of AIDS vaccines containing HIV gag and/or genes from gag as Vaccine Group I. After the first vaccination, a reverse transcriptase-polymerase chain reaction (RT-PCR) is used to detect viremia, and a PCR assay is used to detect the viral vaccine sequences in the sera of the subjects. Furthermore, enzyme-linked immunosorbent assays can be performed to detect host antibody responses or vaccine antigen production. At the same time neopterin, beta2-microglobulin, antibody, cytokine, cytotoxic T lymphocyte (CTL), CD4/CD8 ratios, and lymphocyte proliferation are assessed to analyze humoral and cellular Th1 and Th2 immure responses as necessary (Mellors et al., 1997, Ann. Intern. Med. 126:12:946–54; Sukwit et al., 2001, Asian Pac. J. Allergy Immunol. 19(2):107–13; Galli et al., 2001, J. Biol. Regul. Homeost. Agents., 15:308–13; and Gorse et al., 2001, AIDS Res. Hum. Retroviruses. 17:1175–89). Once positive immune responses against Gag proteins are detected, AIDS vaccines containing vif, vpr, vpu, nef, rev, and tat genes are administered to subjects as Vaccine Group II. The subjects' immune responses against Vif, Vpr, Vpu, Nef, Rev, and Tat proteins are then measured. After the immunized subjects have developed immune responses to the HIV gene products of the vaccines in groups I and II, Vaccine Group 3 is administered, etc.

In order to induce sufficient humoral and cellular immune responses, each vaccine group is administered to subjects on two or three separate occasions. For instance, as shown in Table I, Vaccine Group I is scheduled for administration at weeks 0, 4, and 14 for adults and adolescents, and at weeks 0, 9, 20 for children and babies respectively. Viral proteins of each vaccine group, and specific cytokines or chemokines may be administered to subjects mounting low immune responses to the viral gene products of that group.

In situations in which subjects have previously developed nonspecific immune activation markers, circulating CD8+ T-cells are used as a vaccine-related activation marker for the cellular immune system. The magnitude of the humoral immune response is determined by measuring neutralizing antibodies. The same assays described above are used to detect the immune responses elicited by the AIDS vaccines of Group II. The vaccine(s) of Group III may be given with a Group I and/or Group II boost, or by themselves. The necessity of the boosts is determined from the assays used to measure the humoral and cellular immune responses.

To determine whether the nonhuman subjects developed protective immune responses against HIV/SIV, a vaccine cocktail (Vaccine Groups I, II, and III) is administrated to experimental animals. In a preferred embodiment, high titers of neutralizing antibodies are detected in the absence of viremia and significant changes in activation markers (e.g., neopterin and beta2-microglobulin). A lethal strain of HIV/SIV (Reinhardt et al., 1998, J. Med. Virol. 56:159–167 and Baba et al., 1999, Nat. Med. 5:194–203) is thereafter administrated to the subjects that have developed strong immune responses against HIV/SIV. In particularly preferred embodiments, the vaccinated experimental animals are protected from viral infection. In another preferred embodiment, when an HIV-infected human has been vaccinated, once the vaccination cycle has been completed, the subject develops an immune response and does not develop outward signs and symptoms of AIDS.

TABLE 1

Adult and Adolescent Administration Schedule

| | Vaccine Group | | | |
|---|---|---|---|---|
| Week | I | II | III | IV |
| 0 | + | | | |
| 4 | + | | | |
| 5 | | + | | |
| 9 | | + | | |
| 10 | | | + | |
| 14 | + | | + | |
| 15 | | | | + |
| 19 | | + | | + |
| 20 | | | | |
| 24 | | | + | |
| 29 | | | | + |

TABLE 2

Children and Neonate Administration Schedule

| Week | Vaccine Group | | | |
|---|---|---|---|---|
| | I | II | III | IV |
| 0 | + | | | |
| 9 | + | | | |
| 10 | | + | | |
| 19 | | + | | |
| 20 | + | | + | |
| 29 | | | + | |
| 30 | | + | | + |
| 39 | | | | + |
| 40 | | + | | |
| 49 | | | | |
| 50 | | | | + |

Different Vector Method

The AIDS vaccines used in the different vector method encompass HIV/SIV fragments contained within various viral vectors, various bacterial vectors, and various plasmids (e.g., viral—YFV 17D; bacterial—BCG, plasmid—pCEFL). The vaccination cycle used with these AIDS vaccines varies little from the Common Vector Method, except for the vector choice. Thus, the strategy outlined above for the Common Vector Method also applies to the Different Vector Method.

Multiple Virus Method

It has previously been shown, that HIV-2 infection does not offer protection against subsequent HIV-1 infection (van Der Loeff et al., 2001, AIDS, 15:2303–10). However, the inventor notes that infection with HIV-2 is not equivalent to vaccination with HIV-2 genes or gene products, and that an HIV-1 vaccine may not provide sufficient protection against HIV-2 infection. Thus, for protection against HIV-2 infection and/or disease, vaccines containing HIV-2 genes or epitopes are administered to subjects as Vaccine Group V. It is contemplated that once an immune response against the viral gene products of all five vaccine groups covering most of the HIV-1 and HIV-2 sequences have been elicited, that the vaccinated subjects will be protected from both HIV-1 and HIV-2 infection and/or disease (e.g., AIDS) progression.

Thus, the AIDS vaccines used in the multiple virus method encompasses the vaccines previously described for the common vector and different vector methods, in addition to various genes or gene products from other immunodeficiency virus strains (e.g., HIV-$1_{89\ 6}$) or from related immunodeficiency viruses (e.g., HIV-2). The use of vaccines containing inserts from other strains of HIV/SIV is contemplated to enhance the immune response of the inoculated subjects. For instance, this method encompasses the administration of one or more vaccines containing the HIV-2 env or gag gene to a subject who has already received vaccines containing nearly all of the HIV-1 genome.

Pseudovirus Method

In brief, HIV-1 infects a cell through the binding of viral gp120 to cell receptor CD4. Through membrane fusion initiated by viral gp41, and cellular fusin and CKR-5 proteins, the HIV-1 core particle enters into the cell cytoplasm. Viral RNA is reverse transcribed by its RT into a provirion and integrated into the host-cell genome. The provirion transcription is regulated by transcription factors such as Sp1 and the TATA-binding factors, the members of the NF-kB family, and early form of tat. A full-length viral RNA is produced and spliced into short viral mRNAs, the expression of which is controlled by the rev protein concentration. At a later stage in the infection cycle, HIV-1 particles are packaged at cell surface with the viral env protein. The viral gag and gag-pol proteins are cleaved by the viral protease to generate new virions. (John A. T. Young, PhD, Harvard Medical School The Replication Cycle of HIV-1 HIV InSite Knowledge Base Chapter Published February 1997).

Figure 5:
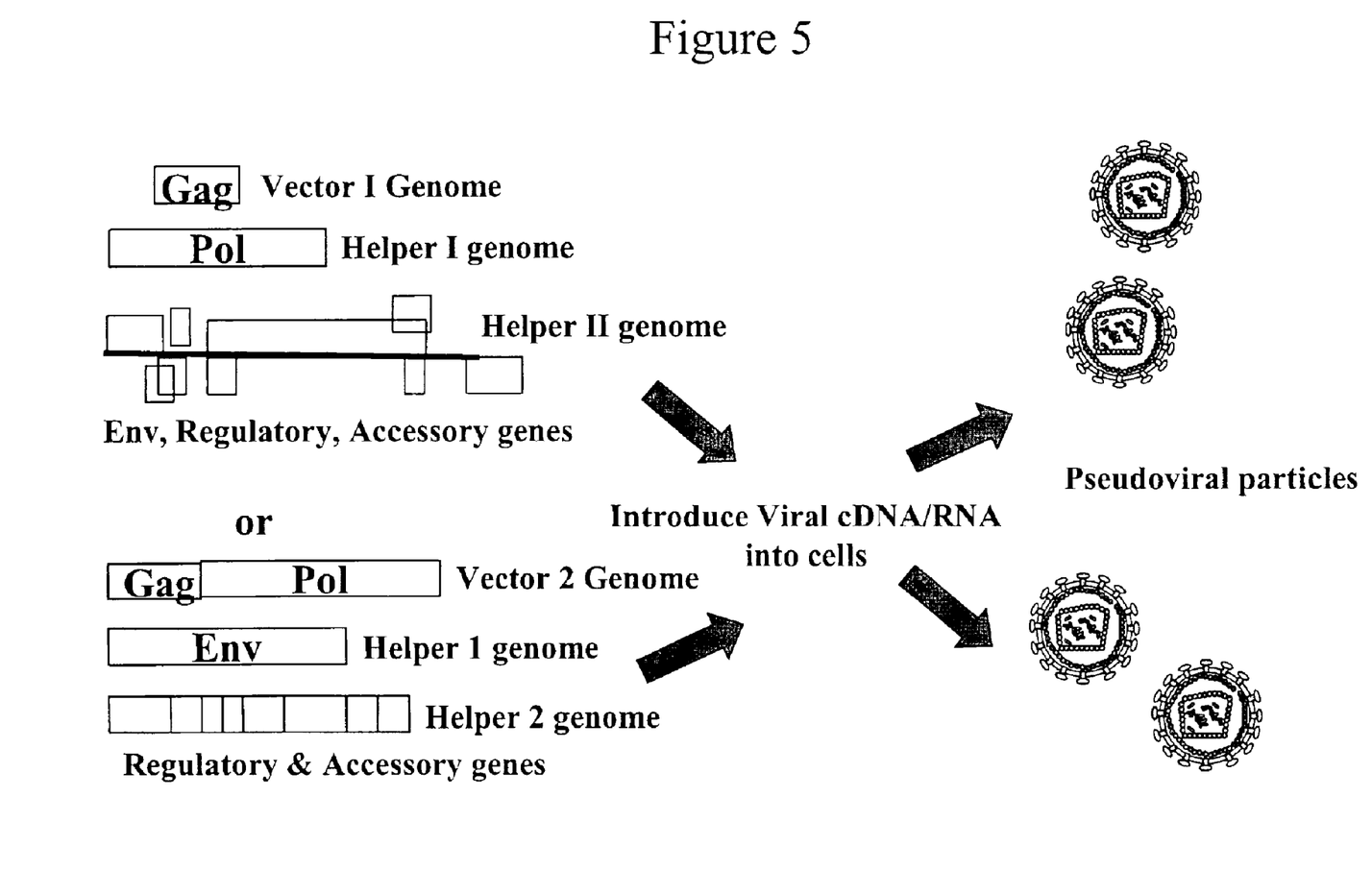

During development of the present invention, a novel approach to the production of an HIV pseudovirus as a suicidal viral particle has been determined (See, FIG. 5). Briefly, a DNA of interest is cloned into three or more plasmids that serve as templates for the in vitro synthesis of recombinant viral HIV RNA. The RNA is subsequently transfected into human or animal cells by electroporation. This expression system includes an in vivo packaging process using at least one or more packaging-deficient helper plasmids to form a pseudovirus particle. This particle lacks many viral genes, as only a partial viral genome is packaged. RNA replication of the HIV pseudovirus is cytoplasmic, and integrase activity is aborted, so there is little risk of viral integration into the host genome. The two-helper system with a vector reduces the possibility of formation of replication-proficient viruses through RNA recombination and thus yielding highly safe pseudoviruses (Smerdou and Liljestrom, 1999, J. Virol. 73:1092–1098). The enzymatic activity of RT may be abolished by mutation to further increase the biosafety of the system. The HIV pseudoviral particle of the present invention contains a complete set of viral proteins, but lacks HIV env, regulatory and accessory genes, as only the gap-pol gene contains the packaging signal necessary for packaging into the pseudoviral particles. In another embodiment, the pol gene is not attached to the gag gene, so that the nascent pseudoviral particles contain only the gag gene. This expression system can also be used in an in vivo packaging process by direct infection of host cells, by employing the cytomegalovirus immediate early promoter.

The HIV pseudoviral particles can "infect" cells through the binding of viral gp120 to host cell CD4, entry into the host cell through membrane fusion, and subsequent disassembly within the host cell cytoplasm. However, without sufficient immunodeficiency virus genes (e.g., no helper constructs) for initiation of the expression of the immunodeficiency virus gene products (e.g., regulatory protein Rev and accessory protein Vpu), the synthesis of viral structural proteins cannot proceed which halts the expression, assembly and/or budding of HIV particles. Thus, replication of a viral progeny in the host cell is impossible and the "infection" is suicidal. The use of this pseudovirus vaccine is contemplated to induce potent immune responses against HIV without risk of infection.

For pseudoviral particle administration, vaccines in each group correspond to different HIV strains (e.g., different isolates or clades). For example, HIV-1 pseudovirus produced from the genes of HIV-$1_{ROD}$ constitutes Vaccine Group I, HIV-1 pseudovirus produced from the genes of HIV-$1_{SF}$ constitutes Vaccine Group II, HIV-2 pseudovirus constitutes Vaccine Group III, etc. The vaccination cycle used with these suicidal particles varies little from the Common Vector Method except for the vaccine gene grouping and vaccine modality. Thus, the strategy outlined above for the Common Vector Method also applies to the Pseudovirus Method.

Administration

For systemic administration, the preferred routes of injection include: intramuscular, intravenous, intraperitoneal, and subcutaneous injections. The route utilized is dependent upon the vaccine formulation. Other preferred routes of administration include: oral, intranasal, intravaginal, intrarectal, and stomacheal. The vaccines of the present invention are formulated in solution, preferably in physiologically compatible buffers such as Hanks' solution, Ringer's solution, saline and phosphate buffered saline, or packaged in liposomes or other time-release agents. Alternatively, the vaccines of the present invention are formulated in a solid or lyophilized form, and dissolved or suspended in a physiologically acceptable solution immediately prior to use.

Animal Models

In a preferred embodiment, the AIDS vaccines are tested in a rhesus macaque model (*Macaca* mulatta). However, other suitable animal models include but not limited to nonhuman primates such as chimpanzees, baboons, marmosets; and other animals such as cows, cats, rabbits, ferrets, and rodents. In preferred embodiments, SIV is used with the rhesus macaque model. However, SHIV, HIV-1, HIV-2, FIV, and BIV, may be also used with this model.

Experimental

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); μM (micromolar); mol (moles); mmol (millimoles); μmol (micromoles); nmol (nanomoles); g (grams); mg (milligrams); μg (micrograms); ng (nanograms); l or L (liters); ml (milliliters); μl (microliters); cm (centimeters); mm (millimeters); μm (micrometers); nm (nanometers); ° C. (degrees Centigrade); U (units), mU (milliunits); min. (minutes); sec. (seconds); % (percent); kb (kilobase); bp (base pair); PCR (polymerase chain reaction), TCID$_{50}$ (50% tissue culture infectious dose); MID$_{50}$ (50% mucosal infectious doses); HIV (human immunodeficiency virus); SIV (simian immunodeficiency virus); CMV (cytomegalovirus); UTS (untranslated sequence); LTR (long terminal repeat); gpp (gag-pol precursor); ATCC (American Type Culture Collection, Manassas, Va.) and Invitrogen (Invitrogen Corporation, Carlsbad, Calif.).

EXAMPLE 1

Virulent Viral Strain and Viral Gene Selection

The raw materials described in this Example are available from the National Institutes of Health AIDS Research and Reference Reagent Program, and or the American Type Culture Collection (ATCC).

In the exemplified approach, bases 1–10277 of SIVmac251/HUT 78 (GenBank Accession Number M19499; and Franchini et al., 1987, Nature 328:539–543) are used as a DNA template. A series of specific primers are designed to amplify target genes: gag (bases 1014–2561), pol (bases 2216–5386), gpp (gap-pol precursor; bases 1014–5386), vif (bases 5316–5960), vpx-vpr (bases 5788–6420), tat (bases 6278–6573 and 8785–8884), rev (bases 6504–6573 and 8585–9041), untranslated sequences (UTS; bases 807–1013 and 6574–8784), env (bases 6580–9225), nef (bases 9059–9802), 5'-LTR (long terminal repeat; bases 1-806), and 3'-LTR (bases 9803–10277). Other genes are also subcloned including: matrix (MA; bases 1136–1446), capsid (CA; bases 1447–2303), nucleocapsid (NC; bases 2304–2450), and gag p6 (bases 2451–2561), viral protease (Pro; bases 2531–2827), integrase (IN; bases 4459–5175), gpp RNAse H (bases 2828–4015), env gp120 (bases 7006–8127) and env gp41 (bases 8125–9225), vpx (bases 5788–6126) and vpr (bases 6127–6420). Other immunodeficiency virus genes are amplified and subcloned in a similar manner. For instance, genes from SIV$_{mac239}$ (GenBank Accession Number M33262; and Rigier and Desrosiers, 1990, AIDS Res. Hum. Retro. 6:1221–32) and from HIV-2$_{89.6}$ (GenBank Accession Number U39362; and Collman et al., 1992, J. Virol. 66:7517–7521 with) are assembled into AIDS vaccines suitable for use with the methods of the present invention. In the same way, various HIV-2 sequences are also obtained for the purposes of vector construction.

EXAMPLE 2

Vaccine Construction

To construct the vaccines for use with the methods of the present invention, immunodeficiency virus genes are manipulated by mutation, recombination, ligation, and deletion, to generate recombinant single genes or multigenes that do not exist in the native HIV or SIV genomes. For some genes, a eukaryotic start codon (e.g., ATG) and/or stop codons (e.g., TAG, TAA, or TGA) are introduced. In some embodiments, the CMV immediate early promoter, the SP6 promoter or the T7 promoter, and/or enhancers are introduced into the vaccine constructs. Additionally, a protease gene, such as the foot and mouth disease virus 2A autoprotease gene, and/or a protease cleavage site is introduced into the vector to permit the synthesis of processed proteins.

The active sites of four enzyme genes from pol (Pro, RT, RNAse H, and IN) are mutated with specific nucleotides in order to produce nonfunctional proteins with conserved three-dimensional structures. Those constructs are made either as a new recombinant pol gene, as chimeras or as single genes. The early tat gene and the late tat gene are amplified separately and ligated side-by-side or as separate genes, or arranged into another multigene containing vpx and vpr genes or the rev gene. In other instances, two or three gp120 genes or two protease genes are fused together and separated by protease cleavage sites such that protein multimers (e.g., dimers, trimers, tetramers) may more readily form upon expression. In some embodiments, cytokine genes, including but not limited to, IL-2, IL-12, and IL-15, Flt3 ligand, are also introduced to enhance adaptive immune responses. The immunodeficiency virus genes amplified in Example 2 are cloned into the TA cloning vector, pCR3.1 (Invitrogen), yielding a first vaccine set. The second vaccine set includes the immunodeficiency virus sequences cloned into adenoviral vector (Cheng et al., 1992, J. Virol. 66:6721–27). The third vaccine set includes the immunodeficiency virus sequences cloned into a second viral vector such as a vesicular stomatitis virus vector (Rose et al., 2001, Cell, 106:539–49) or a Venezuelan equine encephalitis virus vector (Pushko et al., 1997, Virology, 239:389–401). In certain circumstances, other plasmids and vectors are used including, but not limited to pKCB-Z (Sato et al., 1996, Science, 273:352–354; and Kobayashi et al., 1999, Cell Immunol., 198:69–75), bacillus Calmette-Guerin (Kumar et al., 1999, Immunol., 97:515–21), Semliki forest virus (Smerdou and Liljestrom, 1999, J. Virol., 73:1092–1098; Schnell, 2001, FEMS Microbiol. Lett. 200:123–129), and influenza A vector (Ferco et al., 2001, J Virol., 75:8899–908). The identity of all constructs are confirmed by DNA sequencing.

In other embodiments, some genes including but not limited to, gp120, gp41, tat, and rev, are subcloned into the pCEFL plasmid, the pcDNA3.1 plasmid (Invitrogen), or another eukaryotic plasmid, and transfected into an eukaryotic cell line to express viral proteins which can then be purified. Various SIV clones are already available to expedite the subcloning process including for example pGEX-KGvpr (Wang et al., 1995, Virol. 211:102), pCMV-rev (Lewis et al., 1990, J. Virol. 64:1690), pTatC6H-1 (Purvis et al., 1995, AIDS Res. Hum. Retroviruses, 11:443).

To make a suicidal pseudoviral particle as a vaccine, an HIV vector system is made of several recombinants. The first one is the vector replicon, which contains gag and pol genes encoding MA, CA, NC, PR, RT, and IN. The NC gag protein recognizes specific cis-acting RNA packaging signals (Lever et al., 1989, J. Virol., 63:4085–4087; Clavel and Orenstein, 1990, J. Virol., 64:5230–5234; and Aldovini and Young, 1990, J. Virol., 64:1920–1926). Two more helpers are then made. The first helper contains the replication signals and a subgenomic promoter in operable combination with the genes encoding the HIV regulatory proteins, tat, vpr, vpu, vif, rev, and nef. The second helper contains the genes encoding the HIV env proteins gp120 and gp41. RNA is transcribed in vitro from these cDNA helper clones from plasmids containing the cDNA sequences in operable combination with the SP6 or T7 promoter. Alternatively, RNA is transcribed in vivo from these cDNA helper clones from plasmids containing the cDNA sequences in operable combination with eukaryotic promoter. A defined ratio of the three vectors are transfected into cells. The RT encoded by the first vector amplifies all of the viral RNA species. However, only the gag containing RNA is packaged into viral particles because the sequences required for HIV RNA packaging are localized to motifs in NC. Other RNAs produced from helper vectors lack this packaging signal and thus are not incorporated into the viral cores. The HIV LTR is removed from the recombinant vector and helper vectors. Mutations are then introduced into the IN gene to completely inactivate IN to prevent viral integration into the host chromosomes. Additionally, the activity of the RT gene is abolished by mutation if so desired. The use of three independent vector systems also reduces the possibility of recombination among the viral RNA species thus avoiding formation of replication-proficient viruses. Introduction of the three RNA species into specific cell types, results in the formation of a pseudovirus containing all the viral structural proteins, and the unique HIV regulatory proteins in the absence of a complete HIV genome. When this pseudovirus is administered to a subject, only a few proteins encoded by the gag genes are transcribed. The pseudovirus cannot reproduce a complete set of viral proteins (e.g., rev, tat, and env protein) required for viral envelope protein synthesis, and it cannot be repackaged into a viral particle. Additionally, progeny viral particles are not produced because the necessary regulatory and envelope proteins are lacking.

Enhancers, promoters, protease cleavage sites, and/or stop codons are introduced as needed into the helper vectors in order o achieve the desired target expression. These helper vector systems can be modified in various ways. For example, the cytomegalovirus (CMV) immediate early promoter may be utilized to control expression of the HIV genes. Administration of the helper DNA to subjects, results in the high level transcription of the HIV genes as driven by the CMV promoter.

Using the strategy outlined above, genes from several strains of HIV-1 and/or HIV-2 (e.g., viruses differing in cell tropism) can be made into different pseudoviruses. These pseudoviruses are suitable for administration to subjects according to the inoculation scheme provided in Tables 1 and 2. FIG. 5 provides a schematic of this approach.

EXAMPLE 3

AIDS Vaccine Groups

In this Example, at least two sets of AIDS Vaccines are utilized, a first set in a plasmid vector and second set in a viral vector. Each vaccine set is classified into 7 groups:

| | |
|---|---|
| Group I (V-I): | gag (e.g., MA, CA, NC, and p6); |
| Group II (V-II): | regulatory and accessory genes (e.g., early and late tat, nef, vpr, vpx/vpu, vif, and rev); |
| Group III (V-III): | pol, (e.g., Pro, RT RNAse H, and IN); |
| Group IV (V-IV): | 3 envs (e.g., gp120 and gp41 from 3 distinct strains, for example from HIV-1 clades B and C and HIV-2); |
| Group V (V-V): | gpp (e.g., gag-pol precursor); |
| Group VI (V-VI): | gag, pol, and env genes from a another HIV strain; and |
| Group VII (V-VII): | suicidal pseudoviral particles. |

In some embodiments, the pol genes of Groups III, V and VI are mutated to eliminate their enzymatic function while maintaining their three-dimensional structure. Other HIV-1 strains suitable for use with the disclosed methods include but are not limited to HIV-$2_{ROD}$ or HIV-$2_{JSP4-27}$. Regrouping of the genes is within the scope of the present invention, as is the alteration of the gene order within each group.

EXAMPLE 4

Subjects

All experimental nonhuman primates undergo a 6-week quarantine before initiation of the vaccine schedule. Each subject is given three intradermal tuberculin tests, and hematology and serum chemistry profiles are taken. Additionally, a rectal swab is examined for bacterial cultures, feces are examined for occult blood, and ovum and parasite determinations are made. Importantly, the serum of each nonhuman primate subject is screened for antibody reactivity to: SIV, simian type D retrovirus, simian T-cell lymphotropic virus type 1, herpes B virus, and measles virus.

Similarly, all human volunteers are given intradermal tuberculin tests and hematology and serum chemistry profiles are taken. Additionally, a rectal swab is examined for bacterial cultures, feces are examined for occult blood, and ovum and parasite determinations are made. Each human subject is also screened for antibody reactivity to: HIV-1, HIV-2, hepatitis A virus, hepatitis B virus, hepatitis C virus, Kaposi sarcoma-associated herpesvirus, human herpesvirus, cytomegalovirus, human papillomavirus, yeast and fungal infections.

All of experimental animals are subject to the procedures set forth by the revised Public Health Service Policy on Humane Care and Use of Laboratory Animals, the Provision of the Animal Welfare Act, and other applicable laws and regulations.

EXAMPLE 5

AIDS Vaccination Schedule

In a preferred embodiment, vaccines will be administered by the IM route. However, other routes of vaccine administration (e.g., IV, oral, nasal, etc.) find use with the methods and compositions of the present. The DNA dose of each vaccine is equivalent to $5\times10^5$ TCID$_{50}$ (50% tissue culture infectious dose) for oral and nasal routes, $2.25\times10^5$ TCID$_{50}$ for IM route, and $1.5\times10^5$ TCID$_{50}$ for the IV route (Baba et al., 1999, Nat. Med., 104–203). For boosting, 50 μg of each purified protein formulated with MF-59 adjuvant is used (Graham et al., 1996, Ann. Intern. Med., 125:270–279). As shown in Tables 1 and 2, each vaccine group (e.g., DNA and/or corresponding proteins) or placebos are given at 0, 4, and 14 week intervals, to 10–20 adult and adolescent subjects, while an additional 10–20 neonatal subjects (e.g., 1–3 months) and/or 10–20 young (4 month-5 years) subjects receive vaccine or placebo at 0, 9, and 20 week intervals.

The timing of vaccine inoculation is subject to change, as the schedule exemplified in Tables 1 and 2 simply corresponds to one embodiment of the present invention. For instance, the vaccines of Vaccine Group II are not administered to a subject until that subject develops an immune response to the vaccines of Vaccine Group I. Additionally, the vaccine schedule will vary depending upon the species of the subject. For example, the life span of a rhesus macaque is approximately 29 years. This is roughly equivalent to a human life span of 80 years. Thus, for human subjects, the vaccine inoculation schedule may be longer than that shown in Tables 1 and 2.

In other preferred embodiments, an all in one AIDS vaccine is used. For example, a pseudovirus containing a partial viral genome but most of the viral proteins, or vectors containing a cocktail of gag, modified pol (e.g., null mutant), env, and a vif-vpu-vpr-nef chimera, are suitable for use in an abbreviated vaccine regimen.

The AIDS vaccination schedule summarized in Tables 1 and 2 is for prophylactic use in HIV/SIV-seronegative subjects (uninfected). Alternatively, for therapeutic use in HIV/SIV-seropositive subjects, the IN, Pro and RT genes are mutated to eliminate their enzymatic function and/or to avoid integration of the viral genes into the subject's genome.

Molecular adjuvants including, but not limited to the following genes or gene products also find use with the vaccines of the present invention: co-stimulatory molecules (e.g., CD80, CD86), proinflammatory cytokines (e.g., IL-1α, TNF-α, TNF-β), T helper 1 cytokines (e.g., IL-2, IL-12, IL-15 and IL-18), T helper 2 cytokines (e.g., IL-4, IL-5 and IL-10), Flt3 ligand, hematopoietic growth factors (e.g., GM-CSF, SCF), and chemokines (e.g., MIP-1a, MIP-1b, and RANTES). Alternatively, steroids such as methylprednisolone are administrated before or after the pseudovirus or vaccine vector inoculation. Saline is contemplated to be an appropriate control in these instances.

EXAMPLE 6

Viral Challenge

Controls are utilized during testing of the methods and compositions of the present invention. A total of eight different protocols are contemplated to test the efficacy of the vaccines described in Example 3 above: control 1 consists of a placebo only (e.g., corresponding plasmid or other vector without gene(s) of interest); experimental 1 consists of AIDS Vaccines of Group I only; experimental 2 consists of AIDS Vaccines of Groups I and II; experimental 3 consists of AIDS Vaccines of Groups I, II, and III; experimental 4 consists of AIDS Vaccines of Groups I, II, III and IV; experimental 5 consists of AIDS Vaccines of Groups I, II, III, IV and V; experimental 6 consists of AIDS Vaccines of Groups I, II, III, IV, V, and VI; and experimental 7 consists of AIDS Vaccines of Group VII. Additional protocols consisting of different vaccine groups are contemplated to be within the scope of the present invention. For example, the AIDS Vaccines of Groups VI or VII may be administered as part of the experimental 5 protocol. Each protocol is contemplated to consist of from 10 to 40 subjects.

A SIV live virus challenge is used to test the efficacy of the AIDS Vaccines of the present invention, in the rhesus monkey model. In particular, wild type SIV$_{mac239}$ or SIV$_{mac}$251 is administered to each control and experimental subject at months 3, 6, or 12, following completion of the AIDS vaccine regimen (Miller et al., 1997, J. Virol. 71:1911–21; Benson et al., 1998, J. Virol. 72:4170–82). Each control and experimental protocol is divided into 3 sections (e.g., A, B, and C) consisting of 2 to 10 subjects each. In a preferred embodiment, adult male subjects are challenged with a dosage of $10^3$ TCID$_{50}$ via the intravenous route, adult female subjects are challenged with a dosage of $10^5$ TCID$_{50}$ via the intravaginal route, and youth subjects are challenged with a dosage of $10^5$ TCID$_{50}$ via the oral/nasal route, at month 3 (section A), month 6 (section B), or month 12 (section C).

It is contemplated that subjects of experimental protocols 4, 5, 6, and 7 are protected from SIV viral infection and similarly that these regimens are sufficient to protect humans from HIV infection. In contrast, control protocol 1 is contemplated to offer no protection, and experimental protocols 1, 2, and 3 are contemplated to offer only partial protection from immunodeficiency virus infection and/or to delay AIDS development.

EXAMPLE 7

Immune Assays

The AIDS vaccine methods and compositions described herein are contemplated to induce both HIV/SIV-specific humoral and cellular immune responses. One day prior to each experimental or placebo vaccination, serum samples are collected for analysis. Humoral assays such as the measurement of neutralizing antibodies are performed as described (See, Wyand et al., 1996, J. Virol. 70:3724–33; Baba et al., 1999, Nat. Med. 194–203; and Miller et al., 1997, J. Virol. 71:1911–1921). T cell responses including the detection of Th1 and Th2 cytokines (e.g., IL-2, IL-4, IL-10, INF-γ, etc.) are measured by cytokine ELISA or ELISPOT. Additionally, CTL assays, CD4/CD8 ratios and lymphocyte proliferation assays are performed as described (See, Sukwit et al., 2001, Asian Pac. J. Allergy Immunol., 19:107–13; Galli et al., 2001, J. Biol. Regul. Homeost. Agents., 15:308–13; and Gorse et al., 2001, AIDS Res. Hum. Retroviruses., 17:1175–89).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention, which are obvious to those skilled in the relevant fields, are intended to be within the scope of the following claims.

What is claimed is:

1. A composition for inducing an immune response, comprising at least three nucleic acids, each encoding one or more proteins of a first immunodeficiency virus, wherein said nucleic acids together but not individually encode Gag, Pol, Env, regulator and accessory proteins of a first immunodeficiency virus, in the absence of immunodeficiency virus long terminal repeats.

2. The composition of claim 1, wherein said immunodeficiency virus is selected from the group consisting of HIV-1, HIV-2, SIV, and SHIV.

3. The composition of claim 1, wherein at least one of said nucleic acids further comprise at least one gene derived from a second immunodeficiency virus.

4. The composition of claim 1, wherein said at least three nucleic acids are each contained in at least one vector selected from the group consisting of a plasmid vector, an artificial chromosome vector, a bacterial vector, a fungal vector, and a viral vector.

5. The composition of claim 1, wherein said viral Pol protein bears a mutation in its active site.

6. The composition of claim 1, further comprising a pharmaceutically suitable carrier.

7. The composition of claim 1, wherein at least one of said nucleic acids further comprise at least one molecular adjuvant selected from the group consisting of a co-stimulatory molecule, a cytokine, a chemokine and a growth factor.

8. The composition of claim 1, wherein said at least three nucleic acids are suitable for production of a pseudoviral particle comprising structural, regulatory and accessory proteins from said immunodeficiency virus.

9. The composition of claim 8, wherein said pseudoviral particle comprises said immunodeficiency virus gag gene, in the absence of said immunodeficiency virus env gene.

10. The composition of claim 9, wherein said pseudoviral particle is incapable of producing viral progeny.

11. The composition of claim 3, wherein said second immunodeficiency virus is of a different strain than said first immunodeficiency virus.

12. The composition of claim 3, wherein said second immunodeficiency virus is of a different clade than said first immunodeficiency virus.

* * * * *